(12) United States Patent
Iding et al.

(10) Patent No.: US 7,148,362 B2
(45) Date of Patent: Dec. 12, 2006

(54) PROCESS FOR THE PREPARATION OF ENANTIOPURE PYRROLIDIN-2-ONE DERIVATIVES

(75) Inventors: Hans Iding, Rheinfelden (DE); Daniela Krummenacher, Rheinfelden (CH); Beat Wirz, Reinach (CH); Wolfgang Wostl, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 28 days.

(21) Appl. No.: 10/940,155

(22) Filed: Sep. 14, 2004

(65) Prior Publication Data

US 2005/0065204 A1    Mar. 24, 2005

(30) Foreign Application Priority Data

Sep. 18, 2003   (EP) .................................. 03021076

(51) Int. Cl.
*C07D 207/277* (2006.01)
*C07D 207/27* (2006.01)
*C07D 207/12* (2006.01)

(52) U.S. Cl. ...................... 548/531; 548/551; 548/577; 548/572

(58) Field of Classification Search ................ 548/543, 548/531, 577, 551, 572; 514/424, 429, 423
See application file for complete search history.

(56) References Cited

U.S. PATENT DOCUMENTS 4,287,351 A    9/1981   Bourgery et al.

FOREIGN PATENT DOCUMENTS

| EP | 0 393 607 A2 | 10/1990 |
|----|--------------|---------|
| WO | WO 91/00362 A1 | 1/1991 |
| WO | WO 96/40095 | 12/1996 |
| WO | WO 97/33572 | 9/1997 |
| WO | WO 01/34172 | 5/2001 |

OTHER PUBLICATIONS

Lee S.H. et al, XP 004567048, Enzyme and Microbial Technology, vol. 35, No. 5 pp. 429-436 (2004).

Paytash, Peter L. et al, XP 002308874, Journal of the American Chemical Society, 72, pp. 1415-1416 (1950).
Bach, A. W. J., et al. Proc. Natl. Acad. Sci. USA 85: 4934-4938 (1988).
Cesura, A. M., & Pletscher, A., Prog. Drug Research 38:171-297 (1992).
Fowler, C. J., et al. J. Neural. Transm. 49:1-20 (1980).
Benedetti, M. S., et al. Biochem. Pharmacol. 38:555-561 (1989).
Saura, J., et al. Neuroscience 70:755-774 (1995).
Bentué-Ferrer, D., et al. CNS Drugs 6(3): 217-236 (1996).
Gardner, D. M., et al. J. Clin Psychiatry 57 (3):99-104 (1996).
Lam, P. Y. S., et al. Tetrahedron Lett. 43:3091-3094 (2002).
Lam, P. Y. S., et al. Synlett 5:674-676 (2000).
Chan, D. M. T., et al. Tetrahedron Lett. 39:2933-2936 (1998).
Wolfe, J. P., et al. J. Amer. Chem. Soc. 118:7215-7216 (1996).
Zhou, M., & Panchuk-Voloshina, N., Analytical Biochemistry 253:169-174 (1997).
Schlaeger, E. J. & Christensen, K., Cytotechnology vol. 30 pp. 71-83 (1999).

*Primary Examiner*—Kamal A. Saeed
*Assistant Examiner*—Yong Chu
(74) *Attorney, Agent, or Firm*—George W. Johnston; Patricia S. Rocha-Tramaloni; Kimberly J. Prior

(57) ABSTRACT

The present invention relates to a process for the preparation of enantiopure intermediates useful in the synthesis of valuable pharmaceutically active compounds, e.g. MAOB inhibitors, and to novel intermediates of formulae I and II

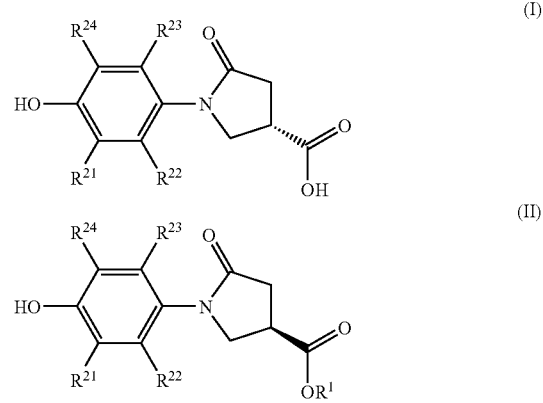

wherein $R^{21}$, $R^{22}$, $R^{23}$ and $R^{24}$ are as defined in the description and claims.

19 Claims, No Drawings

PROCESS FOR THE PREPARATION OF ENANTIOPURE PYRROLIDIN-2-ONE DERIVATIVES

This application claims the benefit of European Application No. 03021076.9, filed Sep. 18, 2003, which is hereby incorporated by reference in its entirety.

More particularly, the present invention provides a process for the preparation of a compound of formula I

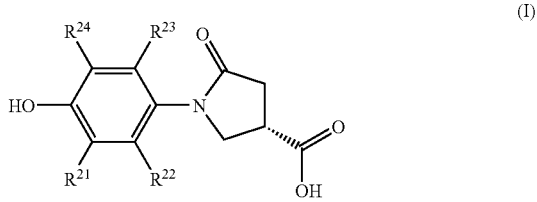

wherein $R^{21}$, $R^{22}$ and $R^{23}$ are each independently hydrogen or halogen; and $R^{24}$ is hydrogen, methyl or halogen;

and/or a compound of formula II

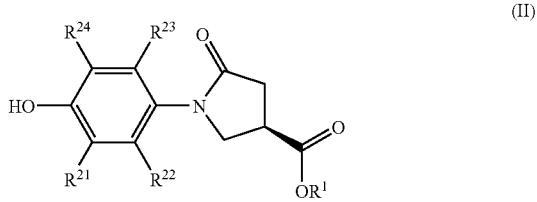

wherein $R^1$ is $(C_1–C_8)$-alkyl, $(C_2–C_4)$-alkenyl or a group of formula A $$R^3(OCH_2CH_2)_n— \quad (A)$$

wherein $R^3$ is hydrogen or $(C_1–C_4)$-alkyl; and n is 1, 2 or 3;

and $R^{21}$, $R^{22}$, $R^{23}$ and $R^{24}$ have the meanings as defined above, comprising contacting a compound of formula III

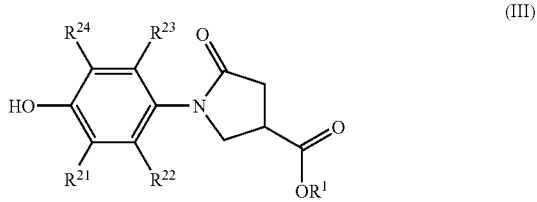

wherein $R^1$, $R^{21}$, $R^{22}$, $R^{23}$ and $R^{24}$ have the meanings as defined above, with a cholesterase derived from yeast.

In the structural formulae presented herein a wedged bond (——◼) denotes that the substituent is above the plane of the paper.

In the structural formulae presented herein a dotted bond (┄┄) denotes that the substituent is below the plane of the paper.

The term "alkyl" as used herein denotes a saturated straight chain or branched hydrocarbon group containing 1 to 8 carbon atoms, such as methyl, ethyl, n-propyl, isopropyl, n-butyl, isobutyl, pentyl, hexyl, heptyl, octyl, including their different isomers. Preferably, the term "alkyl" denotes a straight or branched chain hydrocarbon group containing 1 to 5 carbon atoms which can be unsubstituted or substituted by one or more substituents. Examples for substituents include hydroxy, $(C_1–C_4)$-alkoxy, $(C_3–C_6)$-cycloalkyl, aryl and halogen atoms. Examples for substituted alkyl include 3-hydroxybutyl, 4-methoxybutyl, 3-ethoxypropyl, 3-cyclohexylpropyl, benzyl, 2-phenylethyl, 2-fluoroethyl, 2-chloroethyl, 2,2-dichloroethyl, 3-bromopropyl or 2,2,2-trifluoroethyl and the like.

The term "lower alkyl" as used herein denotes an alkyl group as defined herein having 1 to 4 carbon atoms.

The term "alkoxy" as used herein denotes a residue —O—R, wherein R is a lower alkyl group as defined herein. Examples of alkoxy groups include, but are not limited to, methoxy, ethoxy, isopropoxy, and the like.

The term "cycloalkyl" as used herein denotes a saturated carbocyclic group, containing 3 to 6 carbon atoms. Examples for cycloalkyl include cyclopropyl, cyclobutyl, cyclopentyl and cyclohexyl.

The term "aryl" as used herein denotes a monovalent cyclic aromatic hydrocarbon moiety consisting of a mono aromatic ring. Preferred aryl group is phenyl optionally substituted by one or more fluoro or methyl.

The term "halogen" includes fluorine, chlorine and bromine.

The term "alkenyl" as used herein denotes an unsaturated straight chain or branched hydrocarbon group containing 2 to 4 carbon atoms. Examples for alkenyl include vinyl, allyl, isopropenyl, butenyl and the isomers of butenyl, e.g. 1- or 2-butenyl.

Cholesterases (EC 3.1.1.13) are a group of enzymes of broad specificity also termed cholesterol esterase; cholesteryl ester synthase; triterpenol esterase; cholesteryl esterase; cholesteryl ester hydrolase; sterol ester hydrolase or cholesterol ester hydrolase. They belong to the group of hydrolases which also include esterases, proteases and lipases.

Examples for a cholesterase derived from yeast include a cholesterase derived from the genus *Candida*, e.g. from *Candida cylindracea*. For example, a cholesterase can be obtained by purification from commercially available Lipase MY (Meito Sangyo, Japan), which is obtained from *Candida cylindracea*. The purification may be partial. Examples for commercially available cholesterases derived from yeast is the cholesterase from *Candida cylindracea* offered by Roche Applied Science, Industrial Products, Enzyme Projects, Sandhofer Str. 116, D-68305 Mannheim, Germany, order numbers, e.g. 10129046103 (solid preparation), 0393916 or 0396800 (liquid preparations).

Thus, in one embodiment the invention provides a process wherein the cholesterase derived from yeast is a cholesterase of *Candida cylindracea*.

The cholesterase derived from yeast can be used in a soluble form or in an immobilized form. Various options of how to immobilize an enzyme are known to the skilled artisan.

The enzymatic reaction can take place in an aqueous or in an aqueous-organic system. The substrate, i.e. a compound of formula III, can be applied, e.g., as a suspension. The concentration can be in the range of from 0.5 to 20% overall concentration (w/w), or in the range of from 2 to 10%. The compounds of formula III can be prepared according to known methods from itaconic acid with an optionally substituted aminophenol. In one embodiment the invention provides a process wherein in formula III, $R^{21}$, $R^{22}$, $R^{23}$ and $R^{24}$ are each independently hydrogen or fluorine. In another embodiment the invention provides a process wherein in formula III $R^{21}$, $R^{22}$, $R^{23}$ and $R^{24}$ are hydrogen. In another embodiment the invention provides a process wherein in formula III, $R^1$ is methyl or ethyl.

In one embodiment the present invention provides a process for the preparation of (S)-1-(4-hydroxyphenyl)-5-oxo-pyrrolidine-3-carboxylic acid and an (R)-1-(4-hydroxyphenyl)-5-oxo-pyrrolidine-3-carboxylic acid ester comprising contacting (RS)-1-(4-hydroxyphenyl)-5-oxo-pyrrolidine-3-carboxylic acid ester with a cholesterase derived from yeast.

Common buffer solutions known to be used for biochemical conversions like phosphate buffers or acetate buffers or the like may be used. The buffer concentration can be in the range of up to 1 M, i.e. 1M or less, or in the range of from about 3 mM to about 250 mM.

The enzymatic reaction can take place in the presence of an organic co-solvent. The organic co-solvent can be a water-miscible or a water-immiscible co-solvent. When an organic water-miscible co-solvent is present, its overall concentration can be up to 30%, or up to 25%. The organic water-immiscible co-solvent can be used in an overall concentration at any ratio.

Examples for an organic co-solvent include technically common solvents such as ethers (e.g. tetrahydrofuran, dioxan or tert-butyl methyl ether (TBME)), lower alcohols (e.g. methanol, ethanol, propanol, isopropanol, tert-butanol), esters (e.g. ethyl acetate), polar aprotic solvents (e.g. dimethylsulfoxide, dimethylacetamide, N,N-dimethylformamide or acetone) and alkanes (e.g. heptane) or cycloalkanes (e.g. cyclohexane or methylcyclohexane).

Thus, in one embodiment the invention provides a process wherein the enzymatic reaction takes place in the presence of an organic co-solvent selected from water-immiscible co-solvents, e.g., TBME, heptane; cyclohexane and methylcyclohexane. In another embodiment the invention provides a process wherein the enzymatic reaction takes place in the presence of cyclohexane or methylcyclohexane.

The enzymatic reaction can take place in the presence of a water soluble additive, e.g. in the presence of salts, polyols, polyethylene glycol or derivatives thereof. The additives can have an activating, selectivity triggering or stabilizing effect on the enzyme.

Examples of salts include sodium or potassium chloride, but also other additives e.g. LiSCN, $Na_2SO_4$ and $Mg_2SO_4$. Specifically, the aqueous buffer might contain magnesium ions which are a known activator of the enzyme. The salts can be present in a concentration in the range of up to 1M (i.e., 1M or less), or in the range of up to 0.5 M.

Thus, in one embodiment the invention provides a process wherein the enzymatic reaction takes place in the presence of a magnesium salt.

Examples of polyols include glycerol and sugars. The polyols can be present in a concentration up to 40% (w/w), i.e., 40% or less, of the aqueous phase.

Polyethylene glycols (PEG), optionally as mono- or dimethyl ethers, can be used in a concentration in the range of up to 50% (w/v), or in the range of from 5% to 25%. For example, PEGs in a range of from 4 kD to 6 kD, optionally as mono- or dimethyl ethers, can be used.

After addition of the enzyme, the pH of the reaction mixture can be maintained at a selected pH-value, e.g. the enzymatic reaction can take place at a pH in the range of from pH 3.5 to pH 10.0, or at a pH in the range of from pH 4.0 to pH 8.0, or at a pH in the range of from pH 5.5 to pH 7.0. A constant pH value is maintained by methods known to the skilled artisan, e.g. the controlled addition of a base, e.g. aqueous solutions of sodium or potassium hydroxide or bicarbonate, or the selection of a buffer solution with sufficient buffering capacity.

The enzymatic reaction can take place at a temperature in the range of from 4° C. to 45° C., or at a temperature in the range of from 15° C. to 35° C., or at a temperature in the range of from 26° C. to 32° C.

After termination of the reaction, the compound of formula I and the compound of formula II can be separated by extraction.

For example, the compound of formula II can be worked up conventionally by extraction of the reaction mixture with a suitable organic solvent, e.g. dichloromethane. Upon concentration of the solution the compound of formula II can crystallize, thereby its optical purity can be readily increased.

The antipodal compound of formula I which remained in the aqueous phase can be isolated by subsequent extraction of the aqueous phase at a lower pH value. This can be achieved conventionally by acidification of the retained aqueous phase and filtering off the formed precipitate or by extraction with a suitable organic solvent, e.g. ethyl acetate. Upon concentration of the solution, the compound of formula I can be crystallized and thereby its optical purity can be increased.

Thus, in one embodiment the present invention provides a process for the preparation of a compound of formula I and/or of a compound of formula II comprising contacting a compound of formula III with a cholesterase derived from yeast, and separating the resulting compound of formula I and the resulting compound of formula II by an extraction at a different pH.

If a water soluble additive is co-extracted together with the compound of formula I or formula II, additional extraction steps might be needed to separate the respective reaction product from the additive. Alternatively, adsorber resins or ionic exchange resins might be employed. The selection of the particular extraction regime applied is within the skills of an artisan and depends on the particular nature of the additive. e.g. PEG additive. For example, polyethylene can be separated from the compound of formula I by extraction with e.g. dichloromethane (by co-extraction with the retained compound of formula II), and can subsequently be separated from the retained fraction of compound of formula II by means of ethyl acetate either by solvent change or by trituration/digestion (polyethylene is insoluble under these conditions).

Compounds of formula I and formula II are novel and form another embodiment of the present invention.

The compounds resulting from the process of the invention, i.e. the compound of formula I and the compound of formula II, can be subjected to derivatisation reactions at the carboxylic acid or ester functionality known to the skilled artisan and resulting in, e.g., compounds like carboxamides, N-substituted carboxamides, N,N-disubstituted carboxamides, carboxamidines, N-hydroxy-carboxamidines, carboxylic acid hydroxamides, carboxylic acid hydrazides, carbonitriles, carbaldehydes, ketones, isocyanates, isothiocyanates, carbamates, ureas, N-substituted ureas, N,N-disubstituted ureas, prim., sec. and tert. amines, N-amides, guanidines, aminomethyl-, hydroxymethyl derivatives and ester derivatives.

Examples for such compounds include compounds of formula IVa or formula IVb

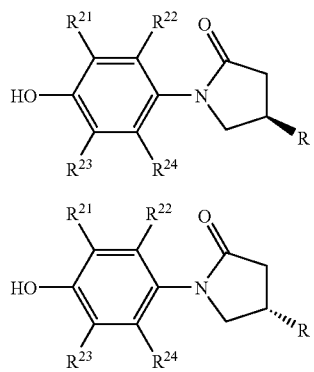

wherein $R^{21}$, $R^{22}$, $R^{23}$ and $R^{24}$ have the meanings as defined for formulae I, II and III, and R is CN, CHO, $CH_2R^4$, $C(O)R^5$, $C(O)NHR^6$, $C(NH)NH_2$, $NHR^7$ or $C(O)OR^8$;

$R^4$ is OH or $NH_2$;

$R^5$ is $(C_1-C_6)$-alkyl;

$R^6$ is H, OH, $NH_2$ or $(C_1-C_6)$-alkyl;

$R^7$ is H or $C(NH)NH_2$; and $R^8$ is $(C_1-C_6)$-alkyl.

The compounds of formulae IVa and IVb are new and also form an embodiment of the present invention.

Racemization of compounds of formula II and, after esterification, of those of formula I for the purpose of recyclization of one of the two enantiomers can be performed using bases, e.g. like alcoholates or 1,8-diazabicyclo[5.4.0]undec-7-ene (DBU).

The compounds resulting from the process of the invention, i.e. the compounds of formula I and the compounds of formula II, and the compounds of formulae IVa and IVb are valuable building blocks and can be used in the synthesis of useful products in the chemical, agricultural and pharmaceutical industry, e.g. in the synthesis of pharmaceutically active compounds, e.g. monoaminooxidase inhibitors which are useful in the treatment of diseases like Parkinson's Disease, Alzheimer's Disease or other diseases of the central nervous system.

For example, the (S)-1-(4-hydroxyphenyl)-5-oxo-pyrrolidine-3-carboxylic acid can be reacted with an alcohol, preferably with methanol or ethanol to yield under acid catalysis the corresponding (S)-1-(4-hydroxyphenyl)-5-oxo-pyrrolidine-3-carboxylic acid ester. The ester can be alkylated by Williamson-ether synthesis using an unsubstituted or substituted benzyl derivative selected from benzylic halides, tosylates, methane sulfonates (mesylates) or trifluoromethane sulfonates (triflates). Bases used can be carbonates, like sodium, potassium or cesium carbonate. Examples for solvents are lower ketones like acetone or 2-butanone. The reaction can take place at a temperature in the range of from 20° C. to reflux temperature. An alternative alkylation method is the Mitsunobu-coupling: An optionally substituted benzylic alcohol is reacted with the phenol in an inert solvent e.g., diethyl ether or tetrahydrofuran, using dialkylazo-dicarboxylates in the presence of phosphines, e.g., tributyl- or triphenyl-phosphine. The hydrolysis of the ester function can be performed by methods known per se like hydrolysis under acidic conditions, e.g. with hydrochloric acid, or basic conditions, e.g. lithium, sodium- or potassium hydroxide in mixtures of alcohols and water as the solvent. The resulting acid can then be submitted to a nucleophilic migration from a carbon to a nitrogen atom, such as e.g. by Hofmann or Curtius rearrangement, via the formation of the corresponding isocyanate. Subsequent treatment of the isocyanate by aqueous acid directly yields the corresponding amine. Treatment of the intermediate isocyanate with suitable alcohols gives the protected amino derivatives in form of the carbamates. For the treatment of the isocyanate, alcohols are selected which yield the typical carbamates used as amine protecting groups, e.g. tert-butoxycarbonyl, benzyloxycarbonyl, or fluorenylmethoxycarbonyl. Methods for the cleavage to the amine are well known from the literature. The further transformation to N-amides can be performed by standard procedures, such as e.g. by reaction with activated acyl derivatives, e.g. acyl halogenides or anhydrides, or by condensation reactions of the acid using e.g. carbodiimides as condensation reagent, thus resulting in compounds like (S)-N-{1-[4-(3-fluoro-benzyloxy)-phenyl]-5-oxo-pyrrolidin-3-yl}-acetamide (Example 10).

The (R)-1-(4-hydroxyphenyl)-5-oxo-pyrrolidine-3-carboxylic acid ester can be alkylated with an unsubstituted or substituted benzyl derivative by Williamson-ether synthesis or Mitsunobu-coupling as described before. The hydrolysis of the ester function can be performed by methods known per se like hydrolysis under acidic conditions, e.g. with hydrochloric acid, or basic conditions, e.g. lithium, sodium- or potassium hydroxide in mixtures of alcohols and water as the solvent. The resulting acid can then be transformed into the corresponding amides by standard procedures. For the reaction with a primary or secondary amine, condensation reagents like carbodiimides, e.g. dicyclohexyl-carbodiimide, or benzotriazol derivatives, e.g. O-(benzotriazol-1-yl)-N,N,N',N'-tetramethyluronium-hexafluorophosphate (HBTU) can be applied to yield compounds like (R)-1-[4-(4-fluoro-benzyloxy)-phenyl]-5-oxo-pyrrolidine-3-carboxylic acid methylamide (Example 9). In the examples the following abbreviations are used: ISN-MS: ion spray negative mass spectroscopy; EI-MS: electron impact mass spectroscopy; NMR: nuclear magnetic resonance spectroscopy; IR: infra red spectroscopy; HPLC: high pressure liquid chromatography; min: minute(s); RT: room temperature; HBTU: O-(benzotriazol-1-yl)-N,N,N',N'-tetramethyluronium-hexafluorophosphate; TBME: tert.-butylmethylether; HV: high vacuum

EXAMPLE 1

Preparation of (RS)-1-(4-Hydroxyphenyl)-5-oxo-pyrrolidine-3-carboxylic Acid Methyl Ester a) A mixture of 2.355 mol of 4-aminophenol and 2.32 mol of itaconic acid was heated gradually: At 60° C., the powder started to become viscous, at 110–120° C. it became liquid and the colour turned to dark brown while the rest of solid material was also dissolved. The exothermic reaction started under boiling, and the temperature rose to 150° C. The sandy product was left to cool down to RT within 1–2 hours. The obtained crude (RS)-1-(4-hydroxyphenyl)-5-oxo-pyrrolidine-3-carboxylic acid was engaged in the next step without further purification or characterisation.

b) The crude (RS)-1-(4-hydroxyphenyl)-5-oxo-pyrrolidine-3-carboxylic acid was dissolved in a mixture of 5000 ml of methanol, 24 ml of concentrated sulfuric acid and 400 ml of 2,2-dimethoxypropane and stirred under reflux for 2 h. The reaction solution was reduced to half of its volume by distillation, then transferred into a 20 l vessel. Under stirring at 40° C., a mixture of 2500 ml of water/ice (1:1) was added. Crystallisation started immediately, and, thereupon, the fine white crystals were collected on a filter funnel. They were washed with a total of 2000 ml of cold water until the filtrate was neutral. The product was dried under reduced pressure to yield 980 g (84% of theory, 2 steps) of (RS)-1-(4-hydroxyphenyl)-5-oxo-pyrrolidine-3-carboxylic acid methyl ester as a white solid; MS: m/e=234 (M+H)$^+$.

In an analogous manner to that described in Example 1 b), the (RS)-1-(4-hydroxyphenyl)-5-oxo-pyrrolidine-3-carboxylic acid ethyl ester was obtained by reaction of the crude (RS)-1-(4-hydroxyphenyl)-5-oxo-pyrrolidine-3-carboxylic acid with ethanol as a white solid; MS: m/e=248 (M−H)$^+$.

EXAMPLE 2

Preparation of (R)-1-(4-Hydroxyphenyl)-5-oxo-pyrrolidine-3-carboxylic Acid Methyl Ester and (S)-1-(4-Hydroxyphenyl)-5-oxo-pyrrolidine-3-carboxylic Acid a) 213.5 mmol of (RS)-1-(4-hydroxyphenyl)-5-oxo-pyrrolidine-3-carboxylic acid methyl ester (98% HPLC) was suspended in 500 ml cyclohexane under moderate stirring. 2.0 l of 3 mM potassium phosphate buffer pH 6.0, containing 0.1 M sodium chloride and 50 mM magnesium sulfate, was added, and the resulting emulsion/suspension was re-adjusted to pH 6.0, and the temperature set to 30° C. Hydrolysis was started by the addition of 201 mg of cholesterase from *Candida cylindracea* (Roche Applied Science, Industrial Products, Enzyme Projects, Sandhofer Str. 116, D-68305 Mannheim, Germany, order number 10129046103, hereinafter: Enzyme) and the pH kept constant at 6.0 by the controlled addition of 0.1 N NaOH solution (pH-stat) under moderate stirring. After a total consumption of 1016 ml of titrating agent (overnight; 48.6% conversion) the reaction mixture was extracted with 3.5 l and 2×2.5 l dichloromethane (turbid phases in the beginning), and subsequently with 3.5 l ethyl acetate (org. phase discarded). The combined dichloromethane phases were dried over sodium sulfate, evaporated and dried under HV to give 22.5 g (95.6 mmol; 44.8%) of (R)-1-(4-hydroxyphenyl)-5-oxo-pyrrolidine-3-carboxylic acid methyl ester as white crystals. *Analytics*: HPLC: >99%. Enantiomeric excess: 96.3% (Chiralpak AD, 250×4.6 mm; 70% hexane+10% 0.1% TFA in hexane+20% ethanol; 1 ml/min; DAD: sig=210.8 nm, ref=360.1 nm; sample application: 0.5 μl of 2 mg/ml 1% TFA in EtOH). [δ]$_D$=−27.7° (c=1.02; EtOH). EI-MS: m/e=235.1 (M; 67), 122.0 (100). $^1$H-NMR (400 MHz; CDCl$_3$): 2.89 (ddd, 2H, —CH$_a$H$_b$—), 3.37 (m, 1H, —CHCOO), 3.78 (s, 3H, COOCH$_3$), 4.03 (ddd, 2H, C(O)NCH$_a$H$_b$), 6.08 (s, 1H, Ph-OH), 6.77, 7.30 (AA'XX', 2×2H, C$_6$H$_4$).

b) The aqueous layer, which was left after the extraction with dichloromethane and ethyl acetate, was set to pH 2.2 with 32% hydrochloric acid and extracted with 3×3.5 l ethyl acetate. The combined organic layers were dried over sodium sulfate, evaporated and dried under HV to give 21.9 g (99.0 mmol; 46.4%) of (S)-1-(4-hydroxyphenyl)-5-oxo-pyrrolidine-3-carboxylic acid as white solid. *Analysis*: HPLC: >99%. Enantiomeric excess: 99.1% (method see above). [δ]$_D$=25.4° (c=1.05; EtOH). EI-MS: m/e=221.1 (M; 57), 122.0 (100). $^1$H-NMR (400 MHz; MeOD): 2.83 (dd, 2H, —CH$_a$H$_b$—), 3.39 (m, 1H, —CHCOO), 4.05 (ddd, 2H, C(O)NCH$_a$H$_b$), 6.79, 7.31 (AA'XX', 2×2H, C$_6$H$_4$).

EXAMPLE 3

Enantioselective Hydrolysis in the Presence of Various Organic Co-Solvents a) To a suspension of 2.13 mmol of (RS)-1-(4-hydroxyphenyl)-5-oxo-pyrrolidine-3-carboxylic acid methyl ester (98%) in 5 ml of TBME, 2 ml of 50 mM magnesium sulfate and 20 ml of 3 mM potassium phosphate buffer pH 6.0 containing 0.1 M sodium chloride and 0.02% sodium azide were added under stirring. The reaction was started by the addition of 10 mg of Enzyme, and the pH maintained at 6.0 by the controlled addition of 0.1 N NaOH. After 10.4 ml consumption (49.9% conversion; 45 h) the reaction mixture was extracted with 3×50 ml dichloromethane, and the combined organic phases were evaporated and submitted to ee-determination. The aqueous phase was acidified to pH 2, extracted with 3×50 ml ethyl acetate. Then, the combined organic phases were evaporated and submitted to ee-determination.

b) To a suspension of 4.25 mmol of (RS)-1-(4-hydroxyphenyl)-5-oxo-pyrrolidine-3-carboxylic acid methyl ester (containing approx. 2% of the respective racemic acid) in 10 ml of organic solvent (see Table), 39 ml of 3 mM potassium phosphate buffer pH 6.0, containing 50 mM magnesium chloride, and 0.1 M sodium chloride were added under moderate stirring, and the temperature set to 28° C. The reaction was started by the addition of 6.5 mg of Enzyme dissolved in 1.0 ml of deionized water, and the pH maintained at 6.0 by the controlled addition of 0.1 N NaOH. After approximately 50% conversion, the reaction mixture was worked up in analogy to Example 3a.

TABLE

Enantioselective hydrolysis in the presence of various organic co-solvents

| solvent | conversion[a] (%) | time (h) | % ee[b] of acid | % ee[b] of ester |
|---|---|---|---|---|
| TBME | 49.9 | 45 | 99.4 | 98.7 |
| cyclohexane | 48.4 | 12 | 96.6 | 98.5 |
| methylcyclohexane | 48.4 | 12 | 97.1 | 99.0 |

[a]according to amount of titrating agent consumed (calculated for 100% pure material)
[b]determination as described in Example 2

EXAMPLE 4

Enantioselective Hydrolysis in the Presence of Various Additives

To a suspension of 4.25 mmol of (RS)-1-(4-hydroxyphenyl)-5-oxo-pyrrolidine-3-carboxylic acid methyl ester (containing approx. 2% of the respective racemic acid) in 10 ml of cyclohexane a solution of additive (see Table) in 3 mM potassium phosphate buffer pH 6.0 containing 50 mM magnesium chloride and 0.1 M sodium chloride, (amount given in Table) was added under moderate stirring and the temperature set to 28° C. The reaction was started by the addition of 6.5 mg of Enzyme dissolved in 1.0 ml of deionized water and the pH maintained at 6.0 by the controlled addition of 0.1 N NaOH. After approximately 50% conversion, the reaction mixture was worked up in analogy to Example 3a).

TABLE

Enantioselective hydrolysis in the presence of various additives

| additive (amount) | buffer (ml) | conversion[a] (%) | time (h) | % ee[b] of acid | % ee[b] of ester |
|---|---|---|---|---|---|
| D-glucose (2.0 g) | 39 | 48.4 | 10 | 91.1 | 98.5 |
| saccharose (2.0 g) | 39 | 47.4 | 14 | 96.0 | 98.3 |
| saccharose (8.0. g) | 39 | 48.0 | 14 | 96.2 | 98.5 |
| polyethylene glycol 200 (2 ml) | 36 | 50.6 | 7 | 94.2 | 98.9 |
| polyethylene glycol 200 (8 ml) | 31 | 48.1 | 12 | 98.0 | 99.5 |

[a]according to amount of titrating agent consumed (calculated for 100% pure material)
[b]determination as described in Example 2

EXAMPLE 5

Enantioselective Hydrolysis in the Presence of Various Salt Additives

To each of the suspensions of 4.25 mmol of (RS)-1-(4-hydroxyphenyl)-5-oxo-pyrrolidine-3-carboxylic acid methyl ester (containing approx. 2% of the respective racemic acid) in 10 ml of cyclohexane, 39 ml of 3 mM potassium phosphate buffer pH 6.0 containing one or two neutral salts (see Table) were added under moderate stirring and the temperature was set to 28° C. The reaction was started by the addition of 6.5 mg of Enzyme, dissolved in 1.0 ml of deionized water, and the pH was maintained at 6.0 by the controlled addition of 0.1 N NaOH. After approximately 50% conversion, the reaction mixture was worked up in analogy to Example 3a).

TABLE

Enantioselective hydrolysis in the presence of various salt additives

| additional salt components | conversion[a](%) | time (h) | % ee[b] of acid | % ee[b] of ester |
|---|---|---|---|---|
| 50 mM MgCl$_2$, 0.1 M NaCl | 48.4 | 12 | 96.6 | 98.5 |
| 50 mM MgCl$_2$ | 49.0 | 10 | 96.1 | 98.6 |
| 100 mM MgSO$_4$ | 47.9 | 9 | 94.5 | 97.6 |

[a]according to amount of titrating agent consumed (calculated for 100% pure material)
[b]determination as described in Example 2

EXAMPLE 6

Enantioselective Hydrolysis at Varying Conditions

To a suspension of (RS)-1-(4-hydroxyphenyl)-5-oxo-pyrrolidine-3-carboxylic acid methyl ester (amount see Table; containing approx. 2% of the respective racemic acid) in organic solvent (see Table), an aqueous buffer solution together with additives (see Table) was added under moderate stirring, and the temperature was set to 28° C. The reaction was started by the addition of Enzyme (amount see Table) dissolved in 1.0 ml of deionized water, and the pH was maintained at 6.0 by the controlled addition of 1.0 N NaOH. After approximately 50% conversion, the reaction mixture was worked up in analogy to Example 3a).

TABLE enantioselective hydrolysis at varying conditions

| substrate (g) | enzyme (mg) | solvent | buffer | additive | conversion[a] (%) | time (h) | % ee[b] of acid | % ee[b] of ester |
|---|---|---|---|---|---|---|---|---|
| 2.0 | 6.5 | CH | PPB[1] | PG (8 ml) | 47.6[c] | 44 | 96.8 | 97.8 |
| 2.5 | 6.5 | CH | PPB[2] | PG (8 ml) | 49.6 | 31 | 94.0 | 96.5 |
| 2.0 | 13 | CH | MgAc$_2$ (23 ml) | PG (16 ml) | 51.2 | 40 | 94.4 | >99 |
| 2.0 | 6.5 | MCH | MgAc$_2$ (35 ml) | PG (4 ml) | ca. 50 | 51 | 94.0 | 97.4 |
| 4.0 | 10 | MCH | MgAc$_2$ (23 ml) | PG (16 ml) | 48.1 | 118 | 93.1 | 97.2 |
| 2.0 | 13 | MCH | MgAc$_2$ (31 ml) | PGM (8 g) | 49.5 | 23 | 94.1 | 93.6 |
| 2.5 | 8.3 | MCH | MgAc$_2$ (35 ml) | PGM (4 g) | 46.3 | 20 | 95.2 | 94.1 |
| 2.5 | 8.3 | MCH | MgAc$_2$ (37 ml) | PGM (2 g) | 47.1 | 15 | 94.7 | 94.8 |
| 3.0 | 10 | MCH | MgAc$_2$ (37 ml) | PGM (2 g) | 46.9 | 28 | 95.7 | 94.6 |

[a]according to amount of titrating agent consumed (calculated for 100% pure material)
[b]determination as described in Example 2
[c]0.1 N NaOH solution was used as titrating agent abbreviations used: CH: cyclohexane (10 ml); MCH: methylcyclohexane (10 ml); PPB[1]: 50 mM MgCl$_2$, 0.1 M NaCl, 3 mM potassium phosphate buffer pH 6.0 (31 ml); PPB[2]: 100 mM MgCl$_2$, 0.1 M NaCl, 3 mM potassium phosphate buffer pH 6.0 (31 ml); MgAc$_2$: 100 mM magnesium diacetate pH 6.0; PG: polyethylene glycol 200; PGM: polyethylene glycol 5000 monomethyl ether

EXAMPLE 7

Enantioselective Hydrolysis with Different Ester

To a suspension of 4.01 mmol of (RS)-1-(4-hydroxyphenyl)-5-oxo-pyrrolidine-3-carboxylic acid ethyl ester in 10 ml of cyclohexane, 39 ml of 3 mM potassium phosphate buffer pH 6.0 containing 50 mM magnesium chloride was added under moderate stirring, and the temperature was set to 28° C. The reaction was started by the addition of 6.5 mg of Enzyme dissolved in 1.0 ml of deionized water, and the pH was maintained at 6.0 by the controlled addition of 0.1 N NaOH. After completion of the reaction, the reaction mixture was worked up in analogy to Example 3a).

TABLE enantioselective hydrolysis with different ester

| Ester | conversion[a] (%) | time (h) | % ee[b] of acid | % ee[b] of ester |
|---|---|---|---|---|
| ethyl ester | 50.2 | 5.1 | 97.8 | 97.0 |

[a]according to amount of titrating agent consumed (calculated for 100% pure material)
[b]determination as described in Example 2

EXAMPLE 8

Preparation of (R)-1-(4-Hydroxyphenyl)-5-oxo-pyrrolidine-3-carboxylic Acid Methyl Ester and (S)-1-(4-Hydroxyphenyl)-5-oxo-pyrrolidine-3-carboxylic Acid a) Preparation of (R)-1-(4-hydroxyphenyl)-5-oxo-pyrrolidine-3-carboxylic acid methyl ester: 106.3 mmol of (RS)-1-(4-hydroxyphenyl)-5-oxo-pyrrolidine-3-carboxylic acid methyl ester (98.2% HPLC; containing 0.2% racemic acid) was suspended in 100 ml methylcyclohexane under moderate stirring. 20.00 g of polyethylene glycol monomethyl ether 5000 was dissolved in 380 ml 0.1 M magnesium acetate pH 6.0 (stirring for 0.5 h; ca. 398 ml volume) and the solution poured to the above suspension. The resulting emulsion/suspension was re-adjusted to pH 6.0, and the temperature was set to 28° C. Hydrolysis was started by the addition of 83 mg of Enzyme, and the pH was kept constant at 6.0 by the controlled addition of 1.0 N NaOH-solution (pH-stat) under moderate stirring. After 17.2 h and a total consumption of 49.64 ml of titrating agent (47.5% conversion), the reaction was stopped by adding 500 ml dichloromethane. The reaction mixture was extracted with 4×500 ml dichloromethane (turbid phases in the beginning) and subsequently with 500 ml ethyl acetate (org. phase discarded). The combined dichloromethane phases were dried over sodium sulfate and evaporated. The residue was triturated overnight in 400 ml ethyl acetate in order to remove insoluble PEG. The suspension was filtered, the filtrate evaporated and the residue recrystallized from dichloromethane to give 11.27 g (47.9 mmol; 45.1%) of (R)-1-(4-hydroxyphenyl)-5-oxo-pyrrolidine-3-carboxylic acid methyl ester as white crystals. Analytics: HPLC: 99.4% ($A_{226nm}$). Enantiomeric excess: 97.8% (method see Example 2). $[\delta]_D$=−29.1° (c=1.04; EtOH). ISN-MS: m/e=294.2 (M+OAc; 70), 234.0 (M-H; 100). IR (Nujol): 3292, 2923, 2854, 1742, 1662, 1615, 1269, 1221, 1029, 832 cm$^{-1}$. $^1$H-NMR (400 MHz; CDCl$_3$): 2.89 (ddd, 2H, —CH$_a$H$_b$—), 3.48 (m, 1H, —CHCOO), 3.78 (s, 3H, COOCH$_3$), 4.03 (ddd, 2H, C(O)NCH$_a$H$_b$), 5.59 (s, 1H, Ph-OH), 6.78, 7.33 (AA'XX', 2×2H, C$_6$H$_4$)

b) Preparation of (S)-1-(4-hydroxyphenyl)-5-oxo-pyrrolidine-3-carboxylic acid: The aqueous phase was set to pH 2.0 with 25% sulfuric acid and extracted with 4×500 ml ethyl acetate. The combined organic phases were dried on sodium sulfate, evaporated and the residue recrystallized from TBME to give 10.49 g (47.4 mmol; 44.6%) of (S)-1-(4-hydroxyphenyl)-5-oxo-pyrrolidine-3-carboxylic acid as white solid. Analysis: HPLC: 99.9% ($A_{226nm}$). Enantiomeric excess: 98.2% (method see above; retention times: (R)-acid: 12.44 min, (S)-acid: 16.25 min). $[\delta]_D$=+25.0° (c=1.01; EtOH). ISN-MS: m/e=220.1 (M-H; 100). IR (Nujol): 3419, 2925, 2854, 2600, 1702, 1628, 1613, 1519, 1277, 1211, 1130, 837 cm$^{-1}$. $^1$H-NMR (400 MHz; DMSO): 2.67 (ddd, 2H, —CH$_a$H$_b$—), 3.31 (m, 1H, —CHCOO), 3.92 (ddd, 2H, C(O)NCH$_a$H$_b$), 6.74, 7.38 (AA'XX', 2×2H, C$_6$H$_4$). According to NMR the product contains ca. 2% of the PEG.

EXAMPLE 9

Preparation of (R)-1-[4-(4-Fluoro-benzyloxy)-phenyl]-5-oxo-pyrrolidine-3-carboxylic Acid Methylamide a) A solution of 4.3 mmol of 4-fluoro-benzylalcohol and 4.7 mmol of triphenylphosphine in 7 ml of tetrahydrofuran was added dropwise at 0° C. to a solution of 4.7 mmol of (R)-1-(4-hydroxyphenyl)-5-oxo-pyrrolidine-3-carboxylic acid methyl ester [Example 2 a) or 8 a)] and 4.7 mmol of diisopropyl azodicarboxylate in 11 ml of tetrahydrofuran. The mixture was left to warm to RT and stirring was continued for 18 hours. After addition of 2 g of silica gel, the reaction mixture was evaporated under reduced pressure. The material obtained was chromatographed on silica gel using first a 2:1-mixture, then a 1:1-mixture of heptane and ethyl acetate as the eluent, yielding (R)-1-[4-(4-fluoro-benzyloxy)-phenyl]-5-oxo-pyrrolidine-3-carboxylic acid methyl ester as a white solid; MS: m/e=344 (M+H)$^+$.

b) A solution of 3.7 mmol of (R)-1-[4-(4-fluoro-benzyloxy)-phenyl]-5-oxo-pyrrolidine-3-carboxylic acid methyl ester in 77 ml of dioxane was treated with 8.64 ml of hydrochloric acid (37%). The mixture was heated at 52° C. for 18 h in a closed flask. The solution was evaporated under reduced pressure to yield the crude acid as a yellowish solid. The crude acid was triturated at −5° C. in 10 ml of ethyl acetate. The solid was collected on a filter funnel and then dried under high vacuum to yield (R)-1-[4-(4-fluoro-benzyloxy)-phenyl]-5-oxo-pyrrolidine-3-carboxylic acid as a white solid; MS: m/e=330 (M+H)$^+$.

c) A solution of 1.82 mmol of (R)-1-[4-(4-fluoro-benzyloxy)-phenyl]-5-oxo-pyrrolidine-3-carboxylic acid in 37 ml of N,N-dimethylformamide was cooled to 0° C., was treated consecutively with 2.0 mmol of triethylamine, 1.82 mmol of HBTU, 2.2 mmol of methylamine hydrochloride, and 2.0 mmol of triethylamine. The ice-bath was removed, and stirring continued at RT. The reaction was stopped after 30 min, and the orange coloured solution was evaporated under reduced pressure. The residue obtained was triturated in 1 ml of ethyl acetate; the white solid product was filtered, thereafter dissolved in dichloromethane; and the solution washed three times with water. The organic phase was dried over sodium sulfate, then evaporated under reduced pressure to yield 409 mg (66% of theory) of the (R)-1-[4-(4-fluoro-benzyloxy)-phenyl]-5-oxo-pyrrolidine-3-carboxylic acid methylamide a white solid. MS: m/e=343 (M+H)$^+$; enantiomeric excess >99.5%.

EXAMPLE 10

Preparation of (S)-N-{1-[4-(3-fluoro-benzyloxy)-phenyl]-5-oxo-pyrrolidin-3-yl}-acetamide a) A solution of 110.6 mmol of 3-fluoro-benzylalcohol and 108.8 mmol of triphenylphosphine in 150 ml of tetrahydrofuran was added dropwise, within 50 min under a nitrogen atmosphere at 0° C., to a solution of 100.5 mmol of (S)-1-(4-hydroxy-phenyl)-5-oxo-pyrrolidine-3-carboxylic acid methyl ester and 100.5 mmol of diisopropyl azodicarboxylate in 200 ml of tetrahydrofuran. The mixture was left to warm to RT and stirring was continued for 18 hours. The mixture was evaporated under reduced pressure. The solid residue was triturated in 400 ml of ether to leave a white solid mainly consisting of the product and triphenylphosphinoxide. After filtration, the solid material was triturated in 100 ml of cold methanol to yield (S)-1-[4-(3-fluoro-benzyloxy)-phenyl]-5-oxo-pyrrolidine-3-carboxylic acid methyl ester as a white solid [MS: m/e=344 (M+H)$^+$] together with traces of triphenylphosphine and diisopropyl hydrazodicarboxylate.

b) A solution of 74.6 mmol of (S)-1-[4-(3-fluoro-benzyloxy)-phenyl]-5-oxo-pyrrolidine-3-carboxylic acid methyl ester in 650 ml of dioxane was treated with 175 ml of hydrochloric acid (37%). The mixture was heated at 50° C. for 18 h in a closed flask. The solution was evaporated under reduced pressure to yield the crude acid as a yellow solid. The crude acid was triturated at 0° C. in 50 ml of ethyl acetate. The solid was collected on a filter funnel and then dried under high vacuum to yield (S)-1-[4-(3-fluoro-benzyloxy)-phenyl]-5-oxo-pyrrolidine-3-carboxylic acid as a yellowish solid; MS: m/e=330 (M+H)$^+$.

c) A solution of 61 mmol of (S)-1-[4-(3-fluoro-benzyloxy)-phenyl]-5-oxo-pyrrolidine-3-carboxylic acid in 300 ml of dioxane was treated with 61 mmol of N-methylmorpholine. Thereafter, the reaction mixture was cooled to −8° C., and 61 mmol of isobutyl chloroformate was added. After stirring for 5 min, a solution of 121 mmol of sodium azide in 40 ml water was added while the temperature rose to 0° C. After stirring for 70 min at 0° C., the suspension was filtered over Dicalite®. The filtrate was diluted with 700 ml of toluene and transferred into a separatory funnel. The organic layer was separated, then washed twice with 250 ml of a saturated solution of sodium hydrogencarbonate and twice with 200 ml of a saturated solution of sodium chloride. Thereafter, the organic layer was dried over sodium sulfate and, after addition of 400 ml of toluene, the solvent and the residual isobutylalcohol were evaporated to end with a volume of about 350 ml. The solution was heated gradually to 80° C. and kept at this temperature for 70 min. After cooling, the solution of the intermediate isocyanate was concentrated to about 300 ml and was added dropwise to a solution of 25.4 ml of hydrochloric acid (37%) in 100 ml of dioxane while heating to 45° C. Finally, after complete addition, the temperature was raised to 60° C. for 1 hour and the hydrochloride already started to precipitate. The mixture was cooled to 0° C., and the solid material formed was collected on a filter funnel. After washing with tert-butylmethylether, the product was dried under high vacuum. There was obtained (S)-4-amino-1-[4-(3-fluoro-benzyloxy)-phenyl]-pyrrolidin-2-one hydrochloride as a white solid. MS: m/e=301 (M+H)$^+$.

d) A suspension of 11.3 mmol of (S)-4-amino-1-[4-(3-fluoro-benzyloxy)-phenyl]-pyrrolidin-2-one hydrochloride in 86 ml of dichloromethane was treated with 23.8 mmol of triethylamine and cooled to 0° C. To this solution, 12.5 mmol of acetylchloride were added and stirring at 0° C. was continued for 15 min. For the working-up, the reaction mixture was extracted twice with 100 ml of water. The organic layer was separated, dried over sodium sulfate and evaporated under reduced pressure. The crude product was triturated in 100 ml of toluene, then the solid collected on a filter funnel. In a second step, the product was triturated in 200 ml of tert-butylmethylether at RT. Again, the solid product was collected on a filter funnel and dried under high vacuum. There was obtained (S)-N-{1-[4-(3-fluoro-benzyloxy)-phenyl]-5-oxo-pyrrolidin-3-yl}-acetamide as a white solid. MS: m/e=343 (M+H)$^+$; enantiomeric excess: >99.5%.

EXAMPLE 11

Preparation of (S)-1-(4-Hydroxyphenyl)-5-oxo-pyrrolidine-3-carboxylic Acid 8.00 g Polyethyleneglycol 6000 was dissolved in 150 mL (100 mM) magnesium acetate buffer pH 6.0 under stirring, and the solution added to a stirred suspension of 10.00 g (42.51 mmol) (RS)-1-(4-hydroxyphenyl)-5-oxo-pyrrolidine-3-carboxylic acid methyl ester (99.7%) in 40 mL methylcyclohexane. The mixture was heated to 28° C. and the pH readjusted to 6.0 with 2 M NaOH. The reaction was started by adding 33.2 mg Candida cylindraceae cholesterase (16.88 kU/g), and the pH was maintained at 6.0 by the controlled addition of 1.0 M NaOH solution under stirring. After a total consumption of 20.35 mL (20.35 mmol) 1.0 M sodium hydroxide solution (after 17.1 h; 47.9% conversion) the reaction mixture was passed through a sintered glass filter. The filtrate spontaneously separated into an aqueous and an organic phase. The aqueous phase was washed with 2×200 mL ethyl acetate to remove uncleaved ester. The aqueous phase was set to pH 4.0 with 25% sulfuric acid and concentrated in vacuo to a volume of ca. 80 mL (bath 60° C.). The solution was cooled to 1° C. (formation of white precipitate/crystals) and the pH set to 1.5 with 25% sulfuric acid. The precipitate/crystals were stirred overnight at 1° C., filtered off on a sintered glass filter (washed with a minimum amount of water) and dried overnight on high vacuum (RT, 6×10$^{-2}$ mbar) to give 4.32 g (19.53 mmol; 45.9%) (S)-1-(4-hydroxyphenyl)-5-oxo-pyrrolidine-3-carboxylic acid. Analysis: HPLC (area A$_{226}$nm): 99.3%, 0.7% ester. 98.9%ee. The product contains 5.3% water (according to Karl Fischer determination) and 2.1% (w/w) PEG (according to NMR).

What is claimed is:

1. A process for the preparation of a compound of formula I

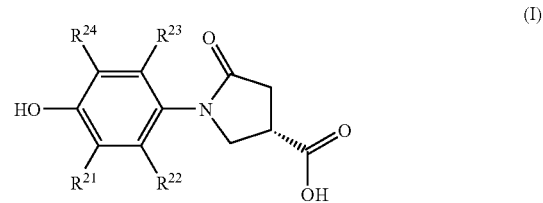

wherein $R^{21}$, $R^{22}$ and $R^{23}$ are each independently hydrogen or halogen; and $R^{24}$ is hydrogen, methyl or halogen;

and/or a compound of formula II

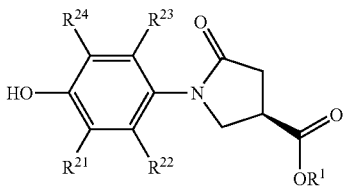

wherein
R¹ is $(C_1-C_8)$-alkyl, $(C_2-C_4)$-alkenyl or a group of formula A $$R^3(OCH_2CH_2)_n—$$ (A)

wherein
R³ is hydrogen or $(C_1-C_4)$-alkyl; and
n is 1, 2 or 3;
and $R^{21}$, $R^{22}$, $R^{23}$ and $R^{24}$ have the meanings as defined above,
comprising contacting a compound of formula III

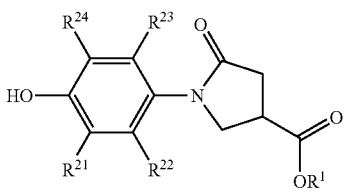

wherein
R¹, $R^{21}$, $R^{22}$, $R^{23}$ and $R^{24}$ have the meanings as defined above,
with a cholesterase derived from yeast in an aqueous or aqueous-organic system.

2. The process according to claim 1, wherein the cholesterase derived from yeast is a cholesterase derived from *Candida cylindracea*.

3. The process according to claim 1, wherein the compound of formula III is applied in a concentration in the range of from 0.5 to 20% overall concentration (w/w).

4. The process according to claim 1, wherein in formula III, $R^{21}$, $R^{22}$, $R^{23}$ and $R^{24}$ are each independently hydrogen or fluorine.

5. The process according to claim 4, wherein in formula III, $R^{21}$, $R^{22}$, $R^{23}$ and $R^{24}$ are hydrogen.

6. The process according to claim 1, wherein in formula III, R¹ is methyl or ethyl.

7. A process for the preparation of (S)-1-(4-hydroxyphenyl)-5-oxo-pyrrolidine-3-carboxylic acid and an (R)-1-(4-hydroxyphenyl)-5-oxo-pyrrolidine-3-carboxylic acid ester comprising contacting an (RS)-1-(4-hydroxyphenyl)-5-oxo-pyrrolidine-3-carboxylic acid ester with a cholesterase derived from yeast in an aqueous or aqueous-organic system.

8. The process according to claim 1, wherein the aqueous or aqueous-organic system comprises a buffer in an amount from about 3 mM to about 1 M.

9. The process of claim 8, wherein the buffer is selected from potassium phosphate buffer or magnesium diacetate.

10. The process according to claim 1, further comprising an organic co-solvent.

11. The process according to claim 10, wherein the co-solvent is tert-butyl methyl ether, cyclohexane or methylcyclohexane.

12. The process according to claim 1, further comprising an additive selected from magnesium salts, polyols, and polyethylene glycol.

13. The process according to claim 12, wherein the salts are present in a concentration of 1M or less.

14. The process according to claim 12, wherein the polyols are present in a concentration of 40% (w/v) or less of the aqueous phase.

15. The process according to claim 12, wherein the polyethylene glycols (PEGs) are selected from PEGs with a molecular weight in the range of from 4 kD to 6 kD, optionally as mono- or dimethyl ethers.

16. The process according to claim 12, wherein the concentration of the polyethylene glycols is 50% (v/v) or less.

17. The process according to claim 1, wherein the reaction takes place at a pH of pH 3.5 to pH 10.

18. The process according to claim 1, wherein the reaction takes place at a temperature in the range of 4° C. to 45° C.

19. The process of claim 17, further comprising extracting the compound of formula II by organic extraction and subsequently extracting a compound of formula I from the aqueous phase at a pH lower than that at which the reaction takes place.

* * * * *